US008263015B2

(12) United States Patent
Raynaud

(10) Patent No.: US 8,263,015 B2

(45) Date of Patent: Sep. 11, 2012

(54) ASEPTIC PACKAGING INSTALLATION WITH ASEPTIC BUFFER ZONES

(75) Inventor: Delphine Raynaud, La Ferte Bernard (FR)

(73) Assignee: Serac Group, La Ferte Bernard (FR)

( * ) Notice: Subject to any disclaimer, the term of this patent is extended or adjusted under 35 U.S.C. 154(b) by 879 days.

(21) Appl. No.: 11/357,989

(22) Filed: Feb. 22, 2006

(65) Prior Publication Data

US 2006/0185321 A1 Aug. 24, 2006

(30) Foreign Application Priority Data

Feb. 23, 2005 (FR) ..................................... 05 01818

(51) Int. Cl.

| | |
|---|---|
| ***B01J 19/00*** | (2006.01) |
| *A61L 2/00* | (2006.01) |
| *A61L 9/00* | (2006.01) |
| *B65B 1/04* | (2006.01) |
| *B65B 3/04* | (2006.01) |
| *B67C 3/02* | (2006.01) |

(52) U.S. Cl. ........ 422/291; 422/292; 422/295; 422/297; 422/300; 422/302; 141/85; 141/93

(58) Field of Classification Search .................. 422/291, 422/295, 292, 297, 300, 302; 141/85, 93
See application file for complete search history.

(56) References Cited

U.S. PATENT DOCUMENTS 4,495,974 A * 1/1985 Pohorski ....................... 141/132
4,597,192 A * 7/1986 Sfondrini et al. ................. 34/66
5,007,232 A * 4/1991 Caudill ........................... 53/426
5,022,165 A * 6/1991 Beswick ........................... 34/62
5,064,614 A 11/1991 Reiss et al.
5,687,542 A * 11/1997 Lawecki et al. ................. 53/122
5,697,203 A * 12/1997 Niwa ............................. 53/510
5,848,515 A * 12/1998 Catelli et al. .................... 53/167
6,189,292 B1 * 2/2001 Odell et al. ...................... 53/425
6,413,481 B1 * 7/2002 Pennekamp et al. .......... 422/302
6,475,435 B1 * 11/2002 Taggart ........................... 422/33

FOREIGN PATENT DOCUMENTS

DE 103 40 876 B3 9/2003
EP 0 758 624 A1 2/1997
EP 0758624 A1 * 2/1997
EP 1 251 085 A1 10/2002
FR 2 800 710 A1 5/2001
FR 2 818 615 A1 6/2002
JP 11342917 A * 12/1999
WO WO 2004/054883 A1 * 7/2004

OTHER PUBLICATIONS

English machine translation of JP 11-342917 A.*

* cited by examiner

*Primary Examiner* — Regina M. Yoo

(74) *Attorney, Agent, or Firm* — Muncy, Geissler, Olds & Lowe, PLLC

(57) ABSTRACT

The aseptic packaging installation comprises a bench under a ceiling, a line of machines mounted on the bench in a packaging zone subjected to a sterile laminar flow traveling vertically from the ceiling at a rate adapted to establish a first pressure in the packaging zone that is higher than a surrounding pressure, an intervention zone adjacent to the packaging zone, and subjected to a one-way flow of clean air travelling vertically from the ceiling of the intervention zone at a rate that is adapted to establish a second pressure in the intervention zone that is lower than the first pressure but higher than the surrounding pressure.

16 Claims, 1 Drawing Sheet

ASEPTIC PACKAGING INSTALLATION WITH ASEPTIC BUFFER ZONES

The present invention relates to an aseptic packaging installation.

BACKGROUND OF THE INVENTION

It is known that in order to ensure long duration conservation of foodstuffs without subjecting them to particular refrigeration conditions, it is necessary for the foodstuff to be conditioned aseptically, i.e. without germs being introduced into the receptacle during the various stages of packaging. In order to ensure that packaging is aseptic, it is known in particular that it is necessary to subject the line of machines used for packaging to sterile conditions that are generally obtained by implementing a laminar flow of filtered air that flows vertically over the line of machines.

For this purpose, existing aseptic packaging installations, such as that described in particular in document FR-A-2 800 710, comprise a cabin that provides a highly aseptic packaging zone around the line of machines, at least one side of the packaging zone being adjacent to an operator zone that is maintained under conditions that are less aseptic than the conditioning zone by providing for air to flow from the packaging zone towards the operator zone through openings in a partition common to the packaging zone and the operator zone. Similarly, document EP 1 251 085 describes enclosures forming a packaging zone at a pressure higher than atmospheric pressure, surrounded by an enclosure at atmospheric pressure forming an operator zone.

It has been found that when a technician seeks to act on the line of machines, either for periodic maintenance, or because of a problem that has arisen during the operation of one of the machines, opening a door providing communication between the operator zone and the packaging zone leads to turbulence that runs the risk of causing less-aseptic air to penetrate from the operator zone into the packaging zone, thereby causing the air in the packaging zone to become less aseptic.

It is also known from document DE 103 40 876 to cause air to flow vertically by disposing a first enclosure at a pressure P1 higher than a pressure P2 that exists in a second enclosure to be disposed one above the other, where P2 is higher than atmospheric pressure. Such an installation does not provide for the possibility of lateral access.

OBJECT OF THE INVENTION

An object of the invention is to provide an aseptic packaging installation that minimizes the risk of pollution in the packaging zone while enabling action to be taken at various points of the installation.

SUMMARY OF THE INVENTION

In order to achieve this object, the invention provides an aseptic packaging installation comprising a bench under a ceiling and a line of machines mounted on the bench in a packaging zone subjected to a sterile laminar flow traveling vertically from the ceiling at a rate adapted to establish a first pressure in the packaging zone that is higher than a surrounding pressure, at least one side of the packaging zone being adjacent to an intervention zone that is subjected to a one-way flow of clean air travelling vertically from the ceiling of the intervention zone at a rate that is adapted to establish a second pressure in the intervention zone that is lower than the first pressure but higher than the surrounding pressure.

Thus, while encouraging sterile air to move from the packaging zone towards the outside, thereby avoiding pollution penetrating into the packaging zone, the one-way flow of air in the intervention zone also avoids turbulence arising in the intervention zone when a door is opened between the packaging zone and the intervention zone, thereby minimizing the risk of the packaging zone being polluted.

In another aspect of the invention, the packaging zone is adjacent on at least one side to an intermediate zone subjected to a one-way flow of clean air flowing at a rate adapted to establish pressure in the intermediate zone that is intermediate between the first pressure and the second pressure. Thus, it is possible to install processor devices in the intermediate zone that need to be aseptic only to a lesser extent, without that harming the degree to which the packaging zone is aseptic, because of the natural movement of air that becomes established from the higher pressure zone towards the zones of progressively lower pressures.

BRIEF DESCRIPTION OF THE DRAWING

Other characteristics and advantages of the invention appear on reading the following description of a particular and non-limiting embodiment of the invention given with reference to the accompanying figures, in which.

DETAILED DESCRIPTION OF THE INVENTION

Figure 2:
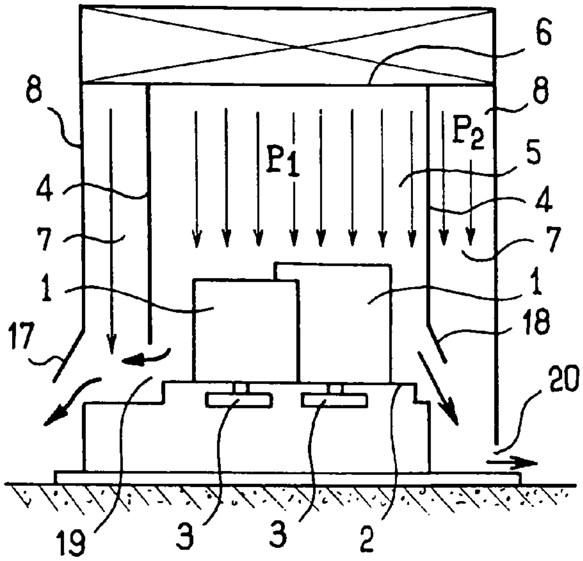
FIG. 2 is a diagrammatic section view on line II-II of FIG. 1.

With reference to the figures, the aseptic packaging installation shown is for packaging a product in receptacles (not shown). In conventional manner, the installation comprises a line of machines 1 such as filler machines, means for heat-sealing capsules, and means for fitting stoppers, all mounted on a bench 2 beneath which there are disposed drive members 3 for driving the machines 1. Walls 4 define a packaging zone 5 subjected to a sterile laminar flow traveling vertically from the ceiling 6 at a rate that is adapted to establish a first pressure P1 in the packaging zone 5 that is higher than the pressure P surrounding the installation. To symbolize the pressure P1, the packaging zone 5 is shaded with fine chain-dotted lines. In order to enable the packaging zone 5 to be pressurized while encouraging a vertical flow of sterile air, the partitions 4 have bottom edges defining a gap 19 that is a few tens of centimeters wide above the bench 2. The first pressure P1 is the result of reaching equilibrium between the feed flow rate through the ceiling and the leakage flow rate via the gaps 19 and any other openings in the side walls of the packaging zone.

On two longitudinal sides of the packaging zone 5, the installation has intervention zones 7 defined by partitions 8 separating the intervention zones from the outside environment.

According to the invention, the intervention zones 7 are also subjected to a flow of clean air, e.g. a flow of sterile air travelling vertically from the ceilings of the intervention zones at a rate that is adapted to establish a second pressure P2 in the intervention zone 7 that is lower than the first pressure P1 in the packaging zone, but higher than the surrounding pressure. The zones at the pressure P2 are shaded in the figure with dotted lines. As for the packaging zone 5, the partitions 8 of the intervention zone 7 define gaps 20 so as to allow air to flow towards the outside and thus encourage air to flow vertically in the intervention zone 7.

Figure 1:
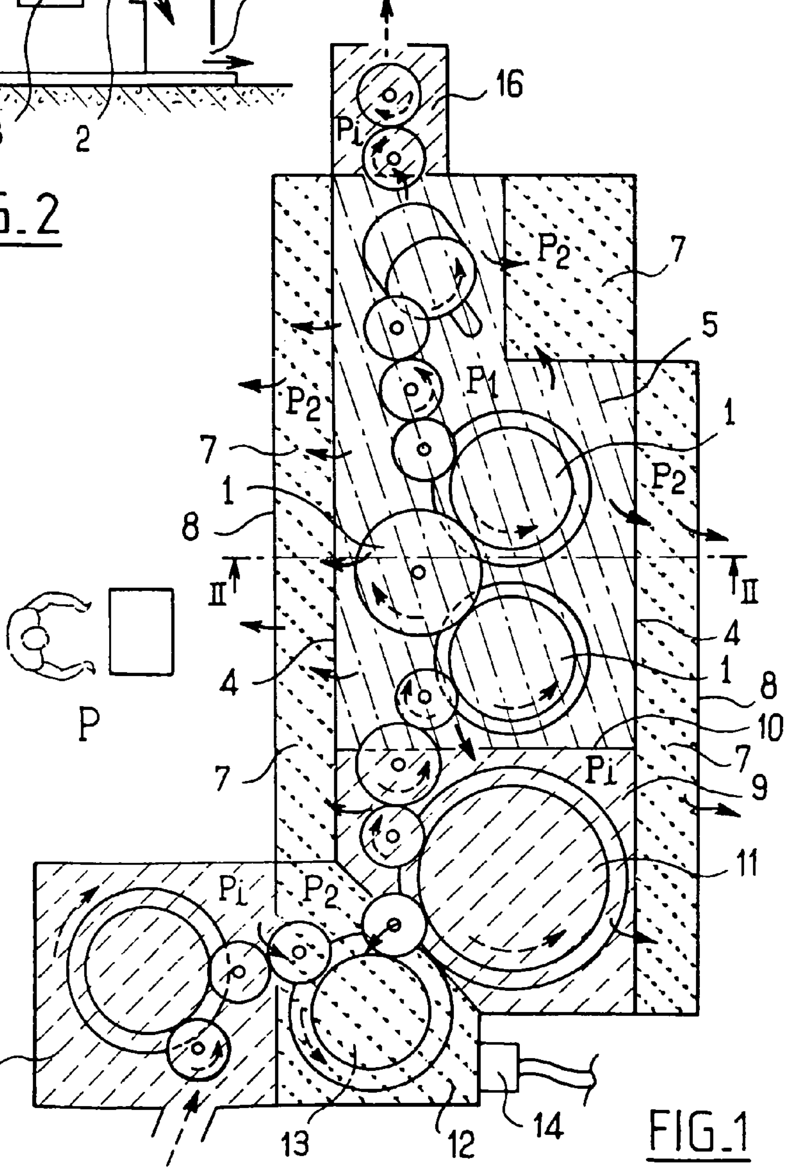
FIG. 1 is a diagrammatic plan view of an installation of the invention.

According to another aspect of the invention, the installation includes an intermediate zone 9 adjacent to the packaging zone 5, upstream therefrom relative to the travel direction of receptacles as represented by dashed-line arrows in FIG. 1. The intermediate zone 9 is subjected to a one-way sterile flow travelling vertically from its ceiling 6 at a rate that is adapted to establish an intermediate pressure Pi in the intermediate zone 9 lying between the first pressure P1 and the second pressure P2. The zones at the pressure Pi are shaded using fine dashed lines. To allow receptacles to pass between the intermediate zone 9 and the packaging zone 5 while encouraging the air flow to travel vertically in each of these zones, the intermediate zone 9 is separated from the packaging zone 5 by an incomplete partition 10. In the example shown, the intervention zone 7 also extends facing the intermediate zone 9 such that because of the order in which pressures decrease between the various zones, the fractional opening in the partition between the intervention zone 7 and the intermediate zone 9 leads to a small movement of air from the packaging zone 5 towards the intermediate zone 9, and from the intermediate zone 9 towards the intervention zone 7, as represented by bold arrows, thereby minimizing any risk of pollution in the packaging zone 5.

In the embodiment shown, the intermediate zone 9 is a drying zone in which there is installed a machine for drying the receptacles. In this embodiment, the drying zone 9 is adjacent to a sterilization zone 12 in which there is installed a sterilization machine 13 operating by atomizing hydrogen peroxide. The sterilization zone 12 is also subjected to a sterile flow travelling vertically from the ceiling of the installation at a rate adapted to establish a pressure in the sterilization zone 12 that is equal to the second pressure P2 in the intervention zones 7.

The installation preferably includes an extractor device 14 which is shown as being beside the sterilization zone 12, although in practice it is preferably mounted at the top thereof.

Upstream from the sterilization zone 12 relative to the direction of receptacle travel, the installation shown has an inlet zone 15, e.g. a de-dusting zone that is likewise subjected to a sterile flow at a rate adapted to establish a pressure equal to the intermediate pressure Pi.

Downstream from the packaging zone 5 relative to the direction of receptacle travel, the installation includes an outlet zone 16 subjected to a flow of air adapted to establish a pressure in the outlet zone 16 similar to the intermediate pressure Pi.

In order to allow access to the intervention zone while minimizing disturbances to the flows, the walls 8 of the intervention zones 8 are preferably fitted with hatches 17. Similarly, to allow local intervention in the packaging zone, the walls 4 of the packaging zone 5 are preferably fitted with hatches 18. The side walls of the packaging zone 5 may also be fitted in conventional manner with sealed sleeves (not shown).

Naturally, the invention is not restricted to the embodiments shown and can be subjected to variations without going beyond the ambit of the invention as defined by the claims.

In particular, although the invention is shown with an installation in which the various zones are subjected to three different pressures, it is possible to make an installation in which the zones are subjected to two different pressures only or on the contrary in which they are subjected to some larger number of different pressures disposed relative to one another in such a manner as to encourage air to move from those zones that need to be the most aseptic towards those zones that can be less aseptic.

In practice, it should be observed that a pressure difference that is small, of the order of about ten Pascals, is preferable in order to minimize the movements of air whenever a partition is opened between two adjacent zones.

What is claimed is:

1. An aseptic packaging installation comprising a bench under a ceiling and a line of machines mounted on the bench in a packaging zone subjected to a sterile laminar flow of filtered air traveling vertically from the ceiling at a rate adapted to establish a first pressure in the packaging zone that is higher than a surrounding pressure, and an intervention zone extending on at least one side of the packaging zone, the intervention zone being subjected to an one-way flow of filtered air travelling vertically from the ceiling of the intervention zone at a rate that is adapted to establish a second pressure in the intervention zone that is lower than the first pressure but higher than the surrounding pressure and is at a temperature permitting access to the packaging zone without interrupting operation of the installation.

2. The aseptic packaging installation according to claim 1, wherein at least one side of the packaging zone is adjacent to an intermediate zone subjected to a flow of filtered air travelling at a rate adapted to establish an intermediate pressure in the intermediate zone that lies between the first pressure and the second pressure.

3. The aseptic packaging installation according to claim 2, wherein the intermediate zone is a drying zone.

4. The aseptic packaging installation according to claim 3, wherein the drying zone is adjacent to a sterilization zone maintained at the second pressure.

5. The aseptic packaging installation according to claim 4, wherein the sterilization zone is fitted with an extractor device.

6. The aseptic packaging installation according to claim 4, wherein an inlet zone is adjacent to the sterilization zone, the inlet zone being maintained at a pressure higher than the second pressure.

7. The aseptic packaging installation according to claim 1, wherein the packaging zone and the intervention zone are separated by a partition including at least one hatch.

8. The aseptic packaging installation according to claim 1, wherein the intervention zone is defined by an outside wall including at least one hatch.

9. The aseptic packaging installation according to claim 8, wherein products travel in a direction along the bench, the intervention zone being free of the bench such that products fail to travel therethrough during operation of the aseptic packaging installation.

10. The aseptic packaging installation according to claim 9, wherein the at least one hatch provides access for maintenance and wherein the products fail to travel through the at least one hatch.

11. The aseptic packaging installation according to claim 1, wherein the packaging zone and the intervention zone include partitions defining gaps allowing air to flow through.

12. The aseptic packaging installation according to claim 1, wherein products travel in a direction along the bench, the intervention zone being free of the bench such that the products fail to travel therethrough during operation of the aseptic packaging installation.

13. The aseptic packaging installation according to claim 1, wherein products travel in a direction along the bench and wherein a line perpendicular to the direction of product travel passes through both the intervention zone and the packaging zone.

14. An aseptic packaging installation comprising a bench under a ceiling and a line of machines mounted on the bench in a packaging zone subjected to a sterile laminar flow of filtered air traveling vertically from the ceiling at a rate adapted to establish a first pressure in the packaging zone that is higher than a surrounding pressure, an intervention zone extending on at least one side of the packaging zone, the intervention zone being subjected to a one-way flow of filtered air travelling vertically from the ceiling of the intervention zone at a rate that is adapted to establish a second pressure in the intervention zone that is lower than the first pressure but higher than the surrounding pressure and is at a temperature permitting access to the packaging zone without interrupting operation of the installation;

wherein ready access to the packaging zone is provided without interrupting operation of the aseptic packaging installation with direct, uninterrupted physical access being provided from ambient environment to the packaging zone.

15. An aseptic packaging installation comprising a bench under a ceiling and a line of machines mounted on the bench in a packaging zone subjected to a sterile laminar flow of filtered air traveling vertically from the ceiling at a rate adapted to establish a first pressure in the packaging zone that is higher than a surrounding pressure, an intervention zone extending on at least one side of the packaging zone, the intervention zone being subjected to a one-way flow of filtered air travelling vertically from the ceiling of the intervention zone at a rate that is adapted to establish a second pressure in the intervention zone that is lower than the first pressure but higher than the surrounding pressure and is at a temperature permitting access to the packaging zone without interrupting operation of the aseptic packaging installation;

wherein ready access to the packaging zone is provided without interrupting operation with an operator being able to touch within the packaging zone while remaining outside the aseptic packaging installation.

16. An aseptic packaging installation comprising a bench under a ceiling and a line of machines mounted on the bench in a packaging zone subjected to a sterile laminar flow of filtered air traveling vertically from the ceiling at a rate adapted to establish a first pressure in the packaging zone that is higher than a surrounding pressure, an intervention zone extending on at least one side of the packaging zone, the intervention zone being subjected to a one-way flow of filtered air travelling vertically from the ceiling of the intervention zone at a rate that is adapted to establish a second pressure in the intervention zone that is lower than the first pressure but higher than the surrounding pressure and is at a temperature permitting access to the packaging zone without interrupting operation of the aseptic packaging installation;

wherein during access to the packaging zone, environment of the packaging zone being free to escape to ambient environment.

* * * * *